United States Patent
Chu et al.

(10) Patent No.: US 8,301,410 B2
(45) Date of Patent: Oct. 30, 2012

(54) VISUAL WEIGHT COMPENSATION

(75) Inventors: Youe-Tsyr Chu, Knoxville, TN (US); Preston S. Baxter, Friendsville, TN (US); Michael E. Galyon, Knoxville, TN (US); Hossein M. Ghorashi, Knoxville, TN (US)

(73) Assignee: Uster Technologies AG, Uster (CH)

( * ) Notice: Subject to any disclaimer, the term of this patent is extended or adjusted under 35 U.S.C. 154(b) by 441 days.

(21) Appl. No.: 12/774,763

(22) Filed: May 6, 2010

(65) Prior Publication Data

US 2011/0276298 A1    Nov. 10, 2011

(51) Int. Cl.
- *G01C 19/40* (2006.01)
- *G01C 17/00* (2006.01)
- *G06F 19/00* (2011.01)
- *G06F 17/40* (2006.01)

(52) U.S. Cl. ....... 702/173; 73/866; 177/25.11; 340/666; 356/237.1; 382/100; 702/81; 702/187; 702/189

(58) Field of Classification Search ............... 73/432.1, 73/865.8, 866; 177/1, 25.11; 340/500, 540, 340/665, 666; 356/237.1, 335, 429; 382/100, 382/141; 702/1, 81, 82, 127, 173, 174, 187, 702/189; 708/100, 105, 200

See application file for complete search history.

(56) References Cited

U.S. PATENT DOCUMENTS

| | | | |
|---|---|---|---|
| 2,995,030 A * | 8/1961 | Feigley, Jr. | 73/61.41 |
| 3,502,162 A * | 3/1970 | Munson | 177/50 |
| 5,321,496 A | 6/1994 | Shofner et al. | |
| 5,533,145 A | 7/1996 | Shofner et al. | |
| 6,567,538 B1 | 5/2003 | Pelletier | |
| 6,615,643 B2 * | 9/2003 | James et al. | 73/73 |
| 6,817,230 B2 * | 11/2004 | James et al. | 73/73 |
| 7,142,693 B2 | 11/2006 | Zhang et al. | |
| 2002/0014116 A1 * | 2/2002 | Campbell et al. | 73/149 |
| 2002/0073776 A1 * | 6/2002 | James et al. | 73/433 |
| 2002/0078532 A1 | 6/2002 | Hosel | |
| 2003/0213290 A1 * | 11/2003 | James et al. | 73/73 |
| 2012/0158342 A1 * | 6/2012 | Chu et al. | 702/101 |

FOREIGN PATENT DOCUMENTS

| | | |
|---|---|---|
| CN | 101403703 A | 4/2009 |
| CN | 201241209 Y | 5/2009 |
| CN | 201255721 Y | 6/2009 |
| CN | 201269857 Y | 7/2009 |
| CN | 101555661 A | 10/2009 |
| EP | 533079 A2 | 3/1993 |
| EP | 0898154 A1 * | 2/1999 |

* cited by examiner

*Primary Examiner* — Edward Cosimano
(74) *Attorney, Agent, or Firm* — Luedeka Neely Group, P.C.

(57) ABSTRACT

A method for determining a corrected weight of a mixed volume, by gravimetrically measuring a total weight of the mixed volume, creating an image of the mixed volume, detecting at least one selected component within the image of the mixed volume, estimating a component weight of the at least one selected component from the image of the mixed volume, and subtracting the component weight from the total weight to yield the corrected weight.

3 Claims, 2 Drawing Sheets

VISUAL WEIGHT COMPENSATION

FIELD

This invention relates to the field of fiber processing. More particularly, this invention relates to estimating the weight of disparate entities in a mixed volume, such as removing the weight of fibers in a volume of trash.

INTRODUCTION

Many quality evaluations have as their basic component a determination of the amount of a contaminant that is found within an amount of the desired material. The fiber processing industry is no different. For example, cotton fibers can be graded based upon how much trash is included within a given volume of fiber. As the term is used herein, "trash" refers to any non-primary-fiber material, such as husks, twigs, leaves, dirt, rocks, and any other non-primary-fiber material that might become mixed into the fiber volume. In the case of cotton fibers for example, trash refers to anything that isn't cotton fiber.

Various methods have been devised to estimate or actually measure the amount of trash within a given mixed volume of fiber and trash. In some methods, the mixed volume is opened in some manner, and the trash is mechanically separated from the fiber. The amount of the trash that is removed from the mixed volume is weighed, and the weight of the trash is used as the basis of the quality evaluation, such as by comparing the weight of the trash to the weight of the mixed volume, or to the weight of separated fiber, or some other such comparison.

Unfortunately, it is relatively difficult to separate the fiber from the trash in a mixed volume. This difficulty results in the process either taking a longer time than desired, or producing an incomplete separation of the mixed volume—with either some amount of trash remaining in the fiber, or some amount of fiber remaining in the trash.

What is needed, therefore, is a system by which problems such as those described above can be reduced, at least to some extent.

SUMMARY OF THE CLAIMS

The above and other needs are met by a method for determining a corrected weight of a mixed volume, by gravimetrically measuring a total weight of the mixed volume, creating an image of the mixed volume, detecting at least one selected component within the image of the mixed volume, estimating a component weight of the at least one selected component from the image of the mixed volume, and subtracting the component weight from the total weight to yield the corrected weight.

In this manner, the weight of the mixed volume can be corrected by electronic means. This means that the mixed volume does not need to be painstakingly separated in some time-consuming or labor-consuming process. Nor does the weight of the mixed volume need to be compromised by the weight of components that are not supposed to be left within the mixed volume. Thus, a corrected weight that accurately represents the desired component or components of the mixed volume can be quickly, easily, and automatically generated.

According to another aspect of the invention there is described a method for determining a trash weight of a mixed volume of trash and cotton fiber, by gravimetrically measuring a total weight of the mixed volume, creating an image of the mixed volume, detecting the cotton fiber within the image of the mixed volume, estimating a cotton fiber weight from the image of the mixed volume, and subtracting the cotton fiber weight from the total weight to yield the trash weight within the mixed volume.

According to yet another aspect of the invention there is described an apparatus for determining a corrected weight of a mixed volume, with a gravimetric scale for measuring a total weight of the mixed volume, a sensor for creating an image of the mixed volume, and a processor for detecting at least one selected component within the image of the mixed volume, estimating a component weight of the at least one selected component from the image of the mixed volume, and subtracting the component weight from the total weight to yield the corrected weight.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
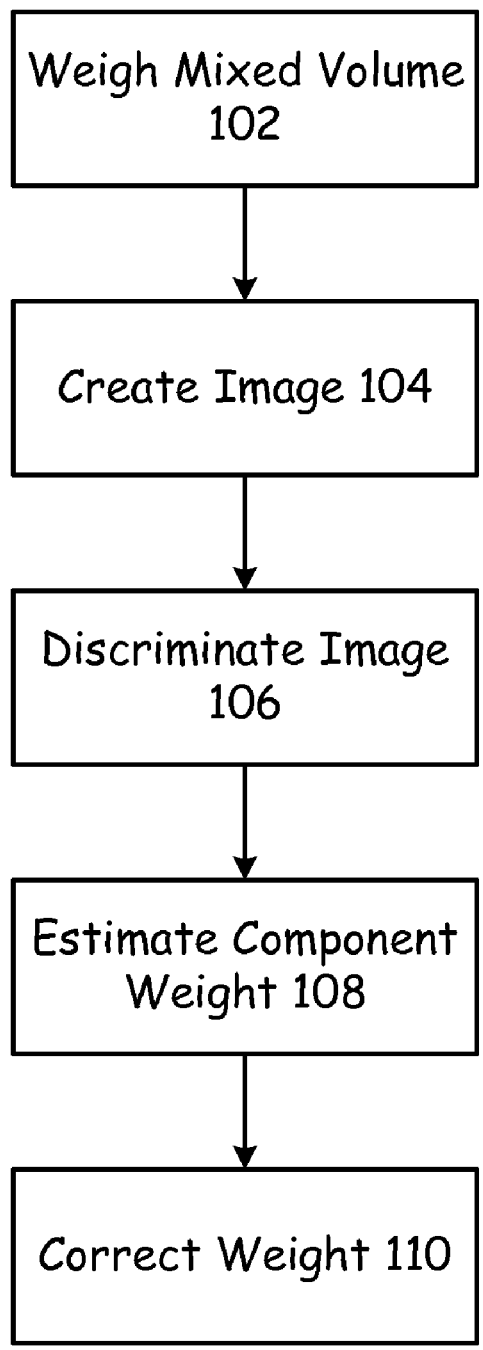
FIG. 1 is a flow-chart of a method according to an embodiment of the present invention.

With reference now to FIG. 1, there is depicted a flow-chart of a method 100 for correcting the weight of a mixed volume of material according to an embodiment of the present invention. The mixed volume is weighed, as given in block 102. This weight can be accomplished in a variety of different ways. For example, the mixed volume can be directly weighed with a gravimetric device like a scale, or weighed with a balance. Whatever method is used, this initial weight of the mixed volume is designated herein as the total weight.

An image is then created of the mixed volume, as given in block 104. In some embodiments, the mixed volume is scattered across a surface, such that all components of the mixed volume can be readily seen from one direction, such as from above the mixed volume. In this manner, the individual components of the mixed volume are not hidden, one by another, from the view-point of the imaging device. In some embodiments a single optical visible-light image from a single imaging device at a single location is used to create the image of the mixed volume. In other embodiments, multiple images from multiple sensors at multiple orientations are created, and in some embodiments wavelengths other than visible wavelengths are used to create the image or images. Other combinations of properties such as these are also contemplated.

Once the image has been obtained, as given in block 104, an algorithm is performed using the image as an input. The algorithm discriminates the various components of the image, as given in block 106. By "discriminates" it is meant that the various components of the mixed volume as depicted in the image are identified as to classification. For example, if the mixed volume is of fiber and trash, then those portions of the image that represent fiber are identified as one classification, and those portions of the image that represent trash are identified as another classification.

The algorithm can be adapted so as to identify more than two classes of components within the mixed volume, as desired. Various threshold levels can be set as desired so as to make the determination as to how a given portion of the image should be classified. Because in some embodiments the mixed volume does not completely cover the surface upon which is it disposed, the algorithm can be set, in those embodiments, to exclude from classification those portions of the surface that are visible in the image, as desired.

Once the image has been classified, as given in block 106, the weight of at least one of the classes of material within the mixed volume is estimated, such as by the algorithm. In some embodiments, the weights of all of the classes of material within the mixed volume are estimated, or the weights of some variable number of the classes are estimated.

For example, returning to the example of a mixed volume of fiber and trash, the weight of the fiber in the mixed volume can be estimated by the algorithm in one embodiment. This can be accomplished by, for example, determining the total volume of fiber within the mixed volume (from the image), and then multiplying that total volume by a presumed or measured fiber density value. A variety of different algorithms for determining the weight of the fiber (or the trash) could be used in different embodiments. These determined weights are designated as the component weights.

After the weight of at least one component of the mixed volume has been estimated, as given in block 108, the corrected weight of the volume is determined, as given in bock 110, such as by subtracting one or more of the component weights from the total weight. For example, in the fiber and trash example, the component weight of the fiber can be subtracted from the total weight, yielding a corrected weight of trash in the mixed volume. Alternately, the component weight of the trash can be subtracted from the total weight, yielding a corrected weight of fiber in the mixed volume.

It is appreciated that some of the steps of the embodiment of the method as described above do not need to be performed in the order as described above or depicted in FIG. 1. For example, measuring the total weight of the mixed volume, as represented in block 102, does not need to be accomplished prior to imaging the mixed volume and estimating the component weight or weights, as given in blocks 104-108. However, the steps of measuring the total weight and estimating at least one component weight do need to be accomplished prior to determining the corrected weight, as given in block 110. In some embodiments, these steps of measuring the total weight and estimating at least one component weight are accomplished substantially simultaneously.

Figure 2:
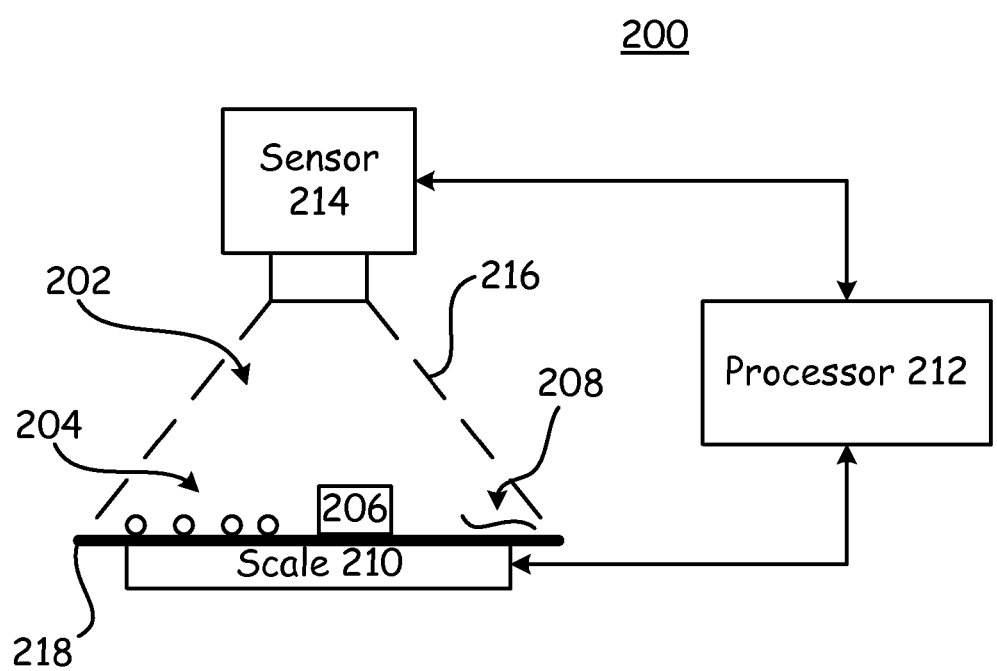
FIG. 2 is a functional block diagram of an apparatus according to an embodiment of the present invention.

With reference now to FIG. 2, there is depicted a functional block diagram of an apparatus 200 according to an embodiment of the present invention. A surface 218 receives the mixed volume 202. In the example as depicted, the mixed volume 202 is comprised of components 204, 206, and 208. For example, the mixed volume 202 might include trash 204, unknown object 206, and fiber 208. A scale 210 measures the total weight of the mixed volume 202, and provides the total weight to the processor 212 for further analysis. The sensor 214 records an image of the mixed volume 202 on the surface 218 within a field of view 216, and provides the image to the processor 212 for further analysis. The processor 212 implements the algorithm as described above, and determines the corrected weight, as desired.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for determining a corrected weight of a mixed volume, the method comprising the steps of:
   gravimetrically measuring a total weight of the mixed volume, creating an image of the mixed volume,
   detecting at least one selected component within the image of the mixed volume,
   estimating a component weight of the at least one selected component from the image of the mixed volume, and
   subtracting the component weight from the total weight to yield the corrected weight.

2. A method for determining a trash weight of a mixed volume of trash and cotton fiber, the method comprising the steps of:
   gravimetrically measuring a total weight of the mixed volume,
   creating an image of the mixed volume,
   detecting the cotton fiber within the image of the mixed volume,
   estimating a cotton fiber weight from the image of the mixed volume, and
   subtracting the cotton fiber weight from the total weight to yield the trash weight within the mixed volume.

3. An apparatus for determining a corrected weight of a mixed volume, the apparatus comprising:
   a gravimetric scale for measuring a total weight of the mixed volume,
   a sensor for creating an image of the mixed volume, and
   a processor for,
      detecting at least one selected component within the image of the mixed volume,
      estimating a component weight of the at least one selected component from the image of the mixed volume, and
      subtracting the component weight from the total weight to yield the corrected weight.

* * * * *